(12) United States Patent
Shifrin

(10) Patent No.: US 9,116,229 B2
(45) Date of Patent: Aug. 25, 2015

(54) ULTRASOUND TRANSMIT BEAMFORMER INTEGRATED CIRCUIT AND METHOD

(75) Inventor: Lazar A. Shifrin, San Jose, CA (US)

(73) Assignee: Microchip Technology Inc., Chandler, AZ (US)

( * ) Notice: Subject to any disclaimer, the term of this patent is extended or adjusted under 35 U.S.C. 154(b) by 2002 days.

(21) Appl. No.: 11/675,517

(22) Filed: Feb. 15, 2007

(65) Prior Publication Data

US 2008/0200809 A1 Aug. 21, 2008

Related U.S. Application Data

(62) Division of application No. 10/886,438, filed on Jul. 6, 2004, now Pat. No. 7,889,787.

(60) Provisional application No. 60/492,588, filed on Aug. 4, 2003.

(51) Int. Cl.
| | |
|---|---|
| H03K 7/08 | (2006.01) |
| H04J 7/00 | (2006.01) |
| G01S 15/10 | (2006.01) |
| G10K 11/34 | (2006.01) |
| G01S 7/52 | (2006.01) |
| A61B 8/00 | (2006.01) |

(52) U.S. Cl.
CPC ............ *G01S 15/102* (2013.01); *G01S 7/5202* (2013.01); *G10K 11/346* (2013.01); *A61B 8/00* (2013.01)

(58) Field of Classification Search
CPC ............ G01S 7/52017; G01S 7/52079; G01S 7/5202; G10K 11/34; H03F 3/217; A61B 5/0068; G02B 21/0048; G06K 2207/1016

USPC .............. 310/311, 317, 316.01, 316.02, 319; 600/437–461

See application file for complete search history.

(56) References Cited

U.S. PATENT DOCUMENTS

| | | | | |
|---|---|---|---|---|
| 5,119,342 | A * | 6/1992 | Harrison et al. | 367/7 |
| 6,819,027 | B2 * | 11/2004 | Saraf | 310/316.01 |
| 2005/0033168 | A1 * | 2/2005 | Shifrin | 600/437 |

* cited by examiner

*Primary Examiner* — Elmer Chao

(74) *Attorney, Agent, or Firm* — Burr & Forman LLP; Ryan M. Corbett

(57) ABSTRACT

The invention provides a novel method of transmit beamforming, which allows compact analog implementation of complex digital algorithms without compromising their features. It is aimed to support envelope shaping, apodization, and phase rotation per channel and per firing. Each of three embodiments represents a complete transmit channel driven by pulse-width modulated (PWM) waveforms stored in a conventional sequence memory. PWM signals controls the transmit pulse envelope (shape) by changing the duty cycle of the carrier. Beamformation data are loaded prior to a firing via serial interface. Under the direction of a controller, the circuitry allows high precision (beyond sampling rate) phase rotation of the carrier. It also provides transmit apodization (aperture weighting), which maintains an optimal trade-off among low sidelobe level and widening of the mainlobe. Implementing such an IC, the manufacturing cost of a high-end ultrasound system can be reduced. Equally, the proposed solution makes the benefits of digital transmit beamformers available to midrange and entry-level machines since it merely requires a modified programming of the sequence memory.

4 Claims, 6 Drawing Sheets

ULTRASOUND TRANSMIT BEAMFORMER INTEGRATED CIRCUIT AND METHOD

RELATED APPLICATION

This patent application claims the benefit of and is a divisional of U.S. patent application Ser. No. 10/886,438, filed Jul. 6, 2004 now U.S. Pat. No. 7,889,787 in the name of Lazar A. Shifrin, and entitled "Ultrasound Transmit Beamformer Integrated Circuit And Method Therefor" which claims the benefit of U.S. Provisional Patent Application having a Ser. No. 60/492,588, filed Aug. 4, 2003 in the name of Lazar A. Shifrin, and entitled "Ultrasound Transmit Beamformer Integrated Circuit And Method Therefor".

BACKGROUND OF THE INVENTION

1. Field of the Invention

This invention relates to coherent ultrasound imaging systems and, in particular, phased array ultrasound imaging systems operating in different scan formats and imaging modes such as, B-, F-, M- and D-modes. Specifically, the invention relates to transmit beamforming and generating ultrasound transmit waveforms.

2. Background of the Invention

An ultrasound scanner with an array transducer comprises a number of identical transmit and receive channels. Acting together, these channels produce transmit and receive beams, respectively. This process is referred as beamforming. It is accomplished by combining transmit/receive signals having variable delay and weight.

There are two mainstream approaches in transmit beamforming: analog and digital. Although prior analog beamformers support different apodization and delay profiles, their precision is inherently limited. Another problem with analog transmit beam formation is insufficient hardware resources to optimize the characteristics of transmit waveforms. Because of this factor, a typical excitation signal looks like a burst of a desired carrier frequency. The waveform shape or envelope is essentially fixed and, therefore, not optimal. The only adjustable parameter is the length of the gate in terms of an integer number of carrier cycles.

There are significant advantages in enhancing the flexibility of a transmit beamformer using digital processing (by way of example, see U.S. Pat. Nos. 4,809,184, 4,896,287, 5,142,649, 5,549,111, 5,970,025, 6,104,673). For that reason, modern high-end ultrasound systems commonly employ digital techniques. The digital transmit beamformer architecture utilizes a plurality of programmable transmit processors each with a source of the desired waveform to be applied to one or more corresponding transducer elements. Since the initially produced waveform is digital, it is converted to analog in order to activate the transducer. The circuits provided this conversion comprises a digital-to-analog converter (DAC) and a transmit amplifier (see U.S. Pat. No. 6,537,216).

Each channel of a digital transmit beamformer is a rather sophisticated signal processing system. Since there is a plurality of transmit channels, the manufacturing cost, power dissipation and space constraints per channel are quite tough. The major problems associated with this factor are as follows:
 a) Operating at sampling frequencies within the range of 50-100 MHz, transmit DACs are fairly priced;
 b) Conventionally used push-pull class B transmit amplifiers are characterized by low power efficiency.

For the theoretical class B amplifier, an absolute maximum of efficiency is 78%. A known alternative to conventional class B designs is those based on pulse-width modulation (PWM) or class D amplifiers. Such designs use analog signal processing to form the PWM signal by comparing the modulating signal with a high frequency sawtooth or triangle waveform that acts as a carrier. The resulting binary signal of the comparator feeds a suitable set of power switches connected to the power supply. Ideally, the switches dissipate no heat energy, i.e., the theoretical efficiency of class D amplifiers approaches 100%. Having low power dissipation, PWM amplifiers can be effectively integrated. Due to the same reason, class D amplifiers are more preferable in terms of heatsinking. These factors are the forces behind the motivation to develop a class-D transmit power amplifier suitable for ultrasound imaging. For instance, U.S. Pat. No. 6,135,963 entitled "Imaging System with Transmit Apodization Using Pulse-Width Variation" describes a method and apparatus for transmit apodization by controlling the duty cycle of the pulse. However, in view of foregoing consideration, building such a universally usable circuit seems to be problematic, despite today's advanced technology.

To maintain low diffraction sidelobes from a sampled aperture, the error $\Delta\phi$ associated with a finite resolution of the delay profile must be kept small. Generally, the average error should be less than the signal provided by one channel. It leads to $\Delta\phi<24/N$, where N is the number of channels. For N=256, $\Delta\phi<2\pi/32$. Thus, implementing a digital beamformer, one needs a 5-6-Bit resolution DAC simply in order to provide an adequate precision of delay profile. However, in addition to fine focusing, DAC supports apodization and shaping. Evidently, that the resulting amplitude resolution of a channel is supposed to be sufficient to maintain the above tasks altogether. In sum, to support digital transmit beamforming, each transmitter should operate with dynamic range of at least 9 Bit.

As well known (Black, H. S. *Modulation Theory*. New York: Van Nostrand Comp., 1953), in PWM waveform, the duty cycle is directly proportional to the modulating signal. Let $F_S$ denote a sampling rate of the double-sided uniform pulse-width modulation (UPWM). Then, to maintain, for example, a 7-bit amplitude resolution, the carrier frequency, $F_C$, would have to be sampled at $F_S=2\cdot 2^7\cdot F_C$. Thus, for a 10 MHz transducer, the power switches would operate at a sub-nanosecond range. Given a 100-200 Volt pulse amplitude, building such a digital amplifier is quite challenging. Besides, running at higher frequencies, the efficiency of a Class D amplifier would be rather defined by dynamic power dissipation than the on/off switch resistance.

SUMMARY OF THE INVENTION

By way of introduction, the present invention includes a method, a system, and device for ultrasound transmit beamforming.

The general purpose of the invention, which will be described below in greater detail, is to provide a novel method of transmit beamforming that allows for compact analog implementation of complex digital algorithms without compromising their features.

Another purpose of this invention is to provide a new transmit beamformer system that outperforms the prior art by simplicity, versatility, lower cost, and higher power efficiency, while maintaining programmability for carrier frequency, transmit waveform shape, delay and apodization profiles.

BRIEF DESCRIPTION OF THE PREFERRED EMBODIMENTS

In a first aspect, the waveform parameters and beamformation data are encoded differently. In particular, transmit waveform having gradually increased and gradually decreased envelope is approximated by a PWM signal. With reference to the resolution needed for focusing, the required number of pulse-width quantization levels for shaping is less. Consequently, the sampling rate can be reduced. At the same time, being greatly suppressed by the bandpass properties of the transducer and the frequency-dependent attenuation of the propagation medium, course quantization does not effect beamformation.

In the second aspect, beamformation data, i.e., apodization and phase rotation values are binary-coded. These data to be converted to analog.

In the third aspect, pulse-width amplitude modulation (PWAM) is provided. The resulting PWAM signals are originated by said PWM waveforms, which is then amplitude-modulated by the above mentioned analog signals. The two kinds of modulation, PWM followed by AM, constitute an analog multiplier circuit and yield a signal comprising both transmit and beamformation components.

Further aspect and advantages of the invention are discussed below in conjunction with the preferred embodiments.

BRIEF DESCRIPTION OF THE DRAWINGS

The invention will be described with respect to particular embodiments therefrom referring to the following drawings.

DETAILED DESCRIPTION OF PREFERRED EMBODIMENTS

An individual transmit waveform can be represented as an amplitude modulated cosine $$x(t)=E(t)\cdot\cos(2\pi F_C t+\Psi)$$

where $E(t)$ and $\Psi$ are transmit envelope and carrier phase angle (in radians), respectively. For the carrier frequency $F_C$, $\Psi$ corresponds to a focusing time delay, $\tau$, as $$\tau=\Psi/2\pi F_C$$

From trigonometry identity, $$x(t)=E(t)\cdot\cos(2\pi F_C t)\cdot\cos\Psi - E(t)\cdot\sin(2\pi F_C t)\cdot\sin\Psi$$

In essence, the above equation depicts an arbitrary vector decomposed into in-phase and quadrature components. These components are representative of the primary I/Q vectors defined as $$I(t)=E(t)\cdot\cos(2\pi F_C t)$$

$$Q(t)=E(t)\cdot\sin(2\pi F_C t)$$

Finally, $$x(t)=I(t)\cdot\cos\Psi - Q(t)\cdot\sin\Psi$$

As can be seen, there is the step of multiplying applied to the primary I/Q vectors. The multiplication factors are the sine and cosine functions of said phase angle $\Psi$. Therefore, to transmit an arbitrary waveform with a programmable phase of the carrier, the beamformer system should incorporate means for providing the primary vectors, computing sine/cosine values, multiplication, and summation.

As used herein, the term "primary I/Q vectors" refers to a pair of quadrature waveforms aimed to originate a transmit signal. Also as used herein, the term "multiplication factors" stands for a pair of programmable constants having their ratio equal to the tangent function of said phase angle, $\Psi$. Autonomously, those constants are proportional to $\sin\Psi$ and $\cos\Psi$. Their magnitude may characterize amplitude weighting (apodization) of a channel. In operation, the multiplication factors are provided prior to firing.

It has been shown that there are two multiplications by a constant involved in phase rotating. Although high-performance analog multipliers are available, implementation on two wide-band four-quadrant devices per channel is quite expensive. However, encoding a primary vector into a digital PWM signal, the resulting pulse train can be used for amplitude sampling of a analog signal associated with a given multiplication factor. This procedure composes two (I/Q) pulse-width amplitude-modulated signals. Then, the obtained two PWAM signals are summed to produce transmit waveform tuned for fine focusing.

Figure 1:
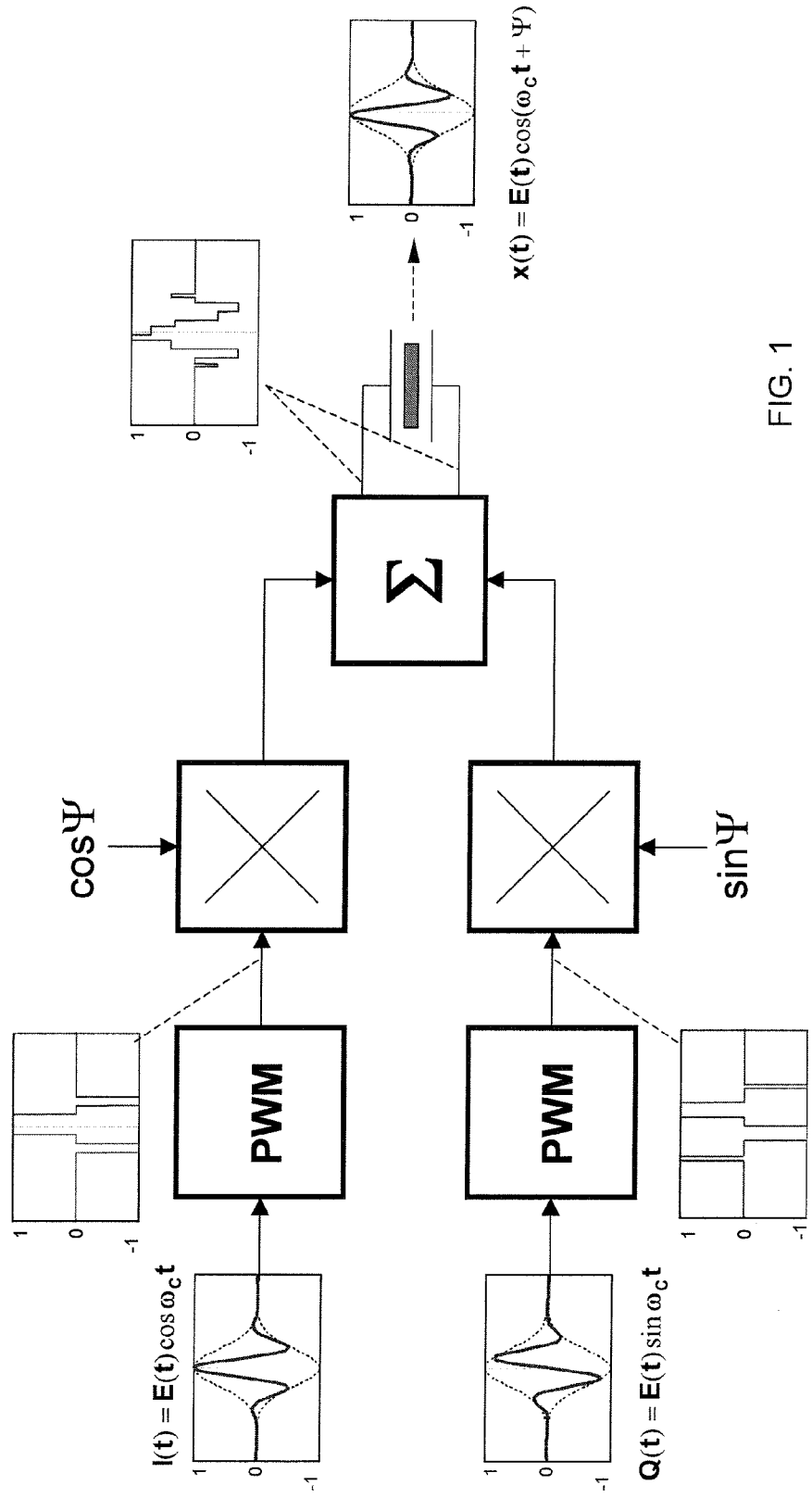
FIG. 1 is a signal flow graph for the proposed method of phase rotation.

Different techniques can be used to provide PWM representation of an analog waveform. Conventionally, PWM sequences are obtained by computing pulse widths in accordance with a modulated analog signal and programming a memory, which is then read out. FIG. 1 shows a signal flow graph for the proposed method of phase rotation regardless of the conversion details.

Figure 2:
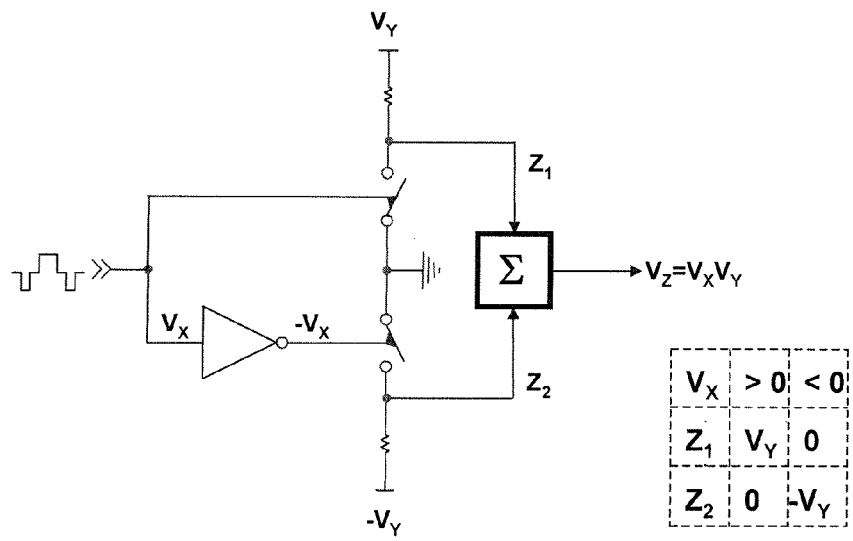
FIG. 2 is a block diagram of the pulse height and width multiplier known in the art.

An apparatus implementing PWAM for multiplication is often referred as "pulse height and width multiplier". FIG. 2 depicts a block diagram of such a circuit as known in the art (see "Electronics Engineers' Handbook", Fink, Donald G. & Christiansen, Donald, 3d edition, McGraw-Hill, 1989, FIG. 13-125). The circuit behavior is illustrated by the accompanying truth table. It will be obvious to those skilled in the art that the switches shown in FIG. 2 are to be bilateral. However, commercially available electronic switches of this kind are characterized by signal-dependent on-resistance that would degrade the accuracy of multiplication.

Figure 3:
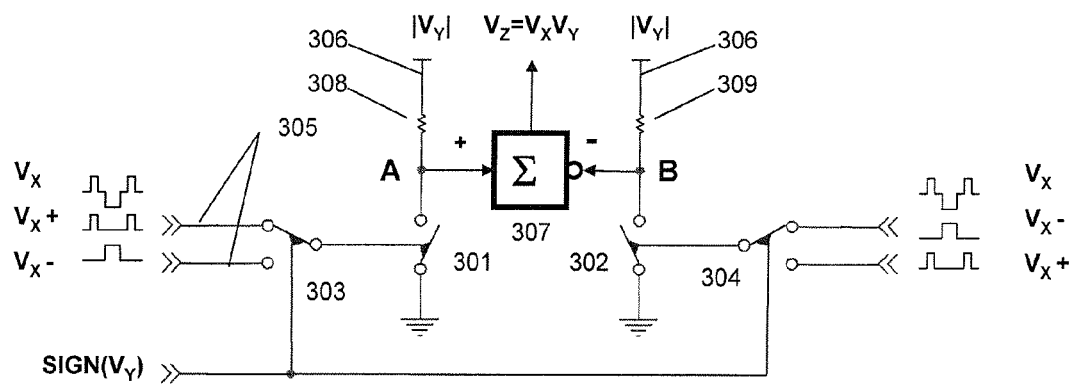
FIG. 3 is a block diagram of a modified height and width multiplier.

The multiplier of FIG. 2 can be modified to eliminate the bilateral switches needed for four-quadrant operation. An improved multiplier topology is shown in FIG. 3. Two important features characterize this topology: analog data are represented into the magnitude/sign format, and a single-ended architecture is replaced by a differential.

The pulse height and width multiplier depicted in FIG. 3 has two input ports: an analog 306 and a digital 305. Said analog 306 and digital 305 ports are single-ended and differential, respectively. Using magnitude/sign format, the analog port 306 operates with unipolar signals, $|V_y|$. Thus, in practice, switches 301, 302 may comprise conventional open-drain (open-collector) devices. Resistance of the pull-up resistors 308, 309 defines the amount of current provided by said switches 301, 302. The PWM pulse train, $V_x$, applied to the port 305 commands the state of said switches 301, 302. To support four-quadrant computation, the phase of said pulse train, $V_x$, is alternated in conjunction with the actual polarity of the analog input signal, $V_y$. In doing so, 2:1 multiplexers (303 and 304) select between the positive and inverted negative portions of the bipolar PWM waveform in response to the sign bit. Having the multiplexers' inputs of the same name driven in reverse, this operation swaps the relative phases of the signals at nodes labeled as A and B. Finally, taking the difference between said nodes, a subtractor 307 provides bipolar PWAM-waveforms.

Figure 7:
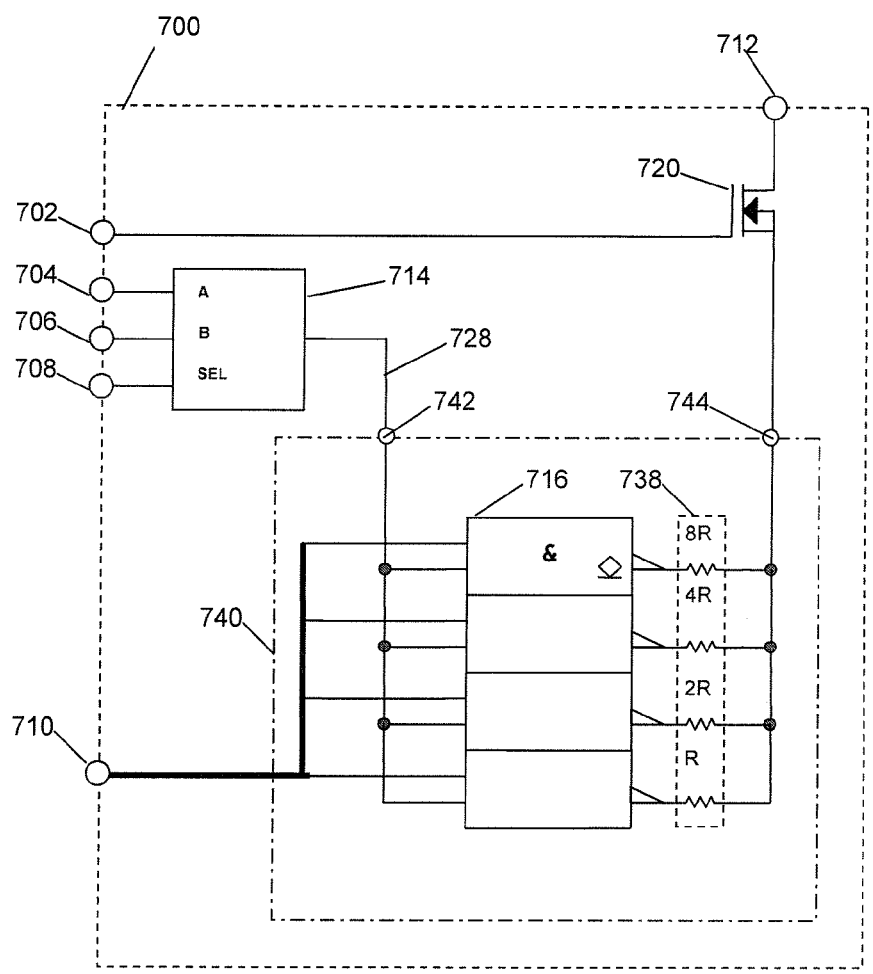
FIG. 7 is a circuit diagram of a programmable current driver implemented within the embodiments.

FIG. 7 depicts one embodiment for the pulse height and width multiplier (PHWM) shown in FIG. 3. In essence, the embodiment represents a programmable current driver comprising a conventional 2:1 multiplexer 714, a digitally programmable resistor (DPR) 740 with enable, a MOS transistor 720, a reference input 702, two clock inputs 704 and 706, a polarity control input 708, a data port 710, and an output 712. The transistor 720 is arranged to have its gate coupled to the reference input 702, drain connected to the output 712, and source connected to a common node 744 of said programmable resistor 740. Multiplexer 714 comprises two selectable inputs, labeled A and B, an output 728 operative to enable the programmable resistor 740, and a control input determining whether the A or B input get routed to the output. The programmable resistor 740 comprises a required plurality of 2-input open-drain NAND gates 716 and resistors 738, said resistors 738 are binary weighted, each resistor 738 is connected between the open-drain output of a gate and the common node 744. A first input of each gate receives a respective bit of a binary word applied to the data port 710; this word represents a desired resistance of the programmable resistor 740.

Referring to FIG. 7, programmable resistance is varied from 8R/15 to 8R. Thus, for a fixed voltage at the gate of the amplifier, the amplitude of the produced current pulses will approach the range of 24 dB. Other dynamic ranges, including lesser or larger ranges may be used. By any means, this range defines attainable amplitude resolution of a PHWM.

All second inputs of each gate are coupled together exhibiting a node 742 and, thus, a logical "1" applied to said node enables conducting of the gates having a logical "1" on their first inputs. Therefore, applying a reference signal to the input 702, the transistor 720 will generate a current pulse whose duration is determined by the width of a signal that drives one of the data inputs. In an alternative embodiment, thermometer coding scheme or its combination with binary techniques may be used. Apparently, the amplitude of this pulse will be directly proportional to said reference signal and inversely proportional to said resistance.

There are several embodiments aimed to implement the proposed method of transmit beamforming. Operatively, these circuits generate transmit waveforms with programmable carrier frequency, envelop shape, fine delay, and apodization. Duplicating identical macrocells, the proposed solutions are suitable for integration. As used herein, the term "transmitter" refers to any circuit or device converting the primary I/Q PWM-signals into transmit waveforms applied to a transducer.

Figure 6:
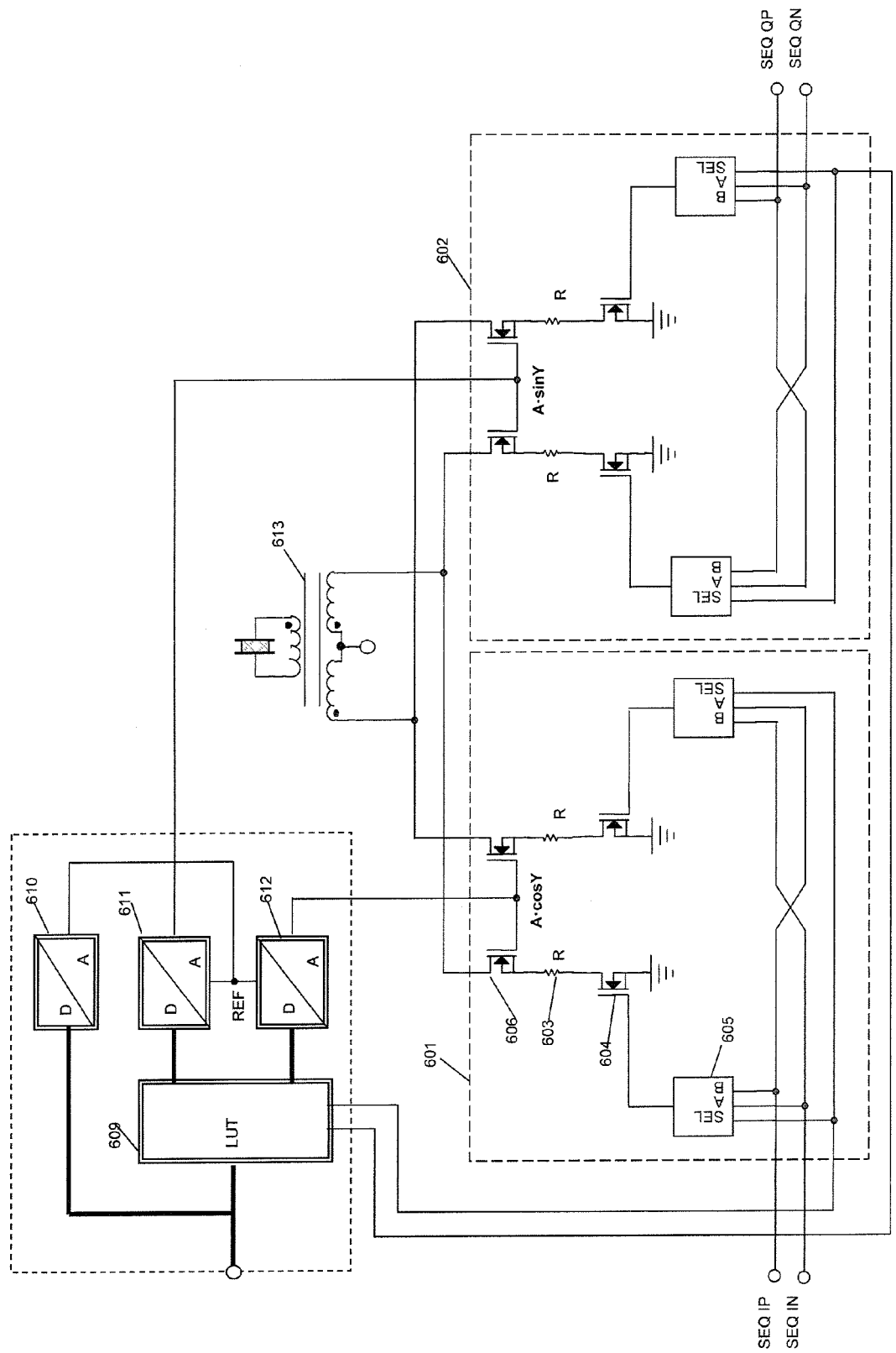
FIG. 6 is a schematic diagram of yet another embodiment of an ultrasound transmitter.

In a first embodiment shown in FIG. 6, there are two identical pulse height and width multipliers, 601 and 602, driving a transformer 613. In operation, said multipliers 601 and 602 receive the primary I/Q PWM-sequences labeled SEQ_IP/N and SEQ_QP/N, respectively. Each of said PHWMs comprises two identical branches operating as an on/off switchable current driver. The switchable current driver includes a resistor 603, an open-drain switch 604, a 2:1 multiplexer 605 and a transistor amplifier 606 connected in a common gate configuration. The gate of the amplifier 606 is fed by a DAC 612. In alternative embodiment, a bipolar transistor in a common base configuration may be used. In other alternative embodiments, different current drivers, such as conventional current mirrors, may be provided. In another alternative embodiment, an open collector switch may be employed. Regardless on the implementation, the current flowing trough the resistor 603 is proportional to the DAC output voltage. This current is turned on/off in response to the multiplexer output aligned with by the PWM pulse train. In consequence, the drain output of the amplifier 606 provides PWM current pulses with programmable amplitude. There is no difference in operation for the other current drivers.

As well known, the common-gate configuration of a transistor amplifier provides high output impedance. Thus, coupling two drain outputs, the fractional currents are summed. In view of that, I/Q drain outputs are connected to the primary winding 613 of the transformer in pairs. The center tap of the primary winding is connected with a high voltage power supply. The secondary winding provides the transmitter output. The transformer may have a step-down or a step-up winding ratio.

There is a transmit controller aimed to support beamformation. The controller comprises a sine/cosine look-up-table (LUT) 609, two multiplying DACs 611, 612, and a conventional DAC 610. In operation, the LUT converts the input value of the phase angle into two digital words representing the sine and cosine function of said phase angle and deliver it to said multiplying DACs. The multiplying DACs provide the multiplication factors for phase rotation in the analog form. The apodization value is directly applied to the DAC 610. Its output provides the reference voltage for both multiplying DACs, 611 and 612. Thus, the amplitude of current pulses generated by said modulators 601, 602 is directly proportional to the product of said phase-rotating and apodization factors.

Since the gate voltage in FIG. 6 is formed as a product of phase rotating and apodization factors, it may have a wide dynamic range. Consequently, the threshold voltage tolerance of the transistor amplifiers may degrade the accuracy of beamformation. In view of that, the second embodiment shown in FIG. 5 introduces a different architecture.

Figure 5:
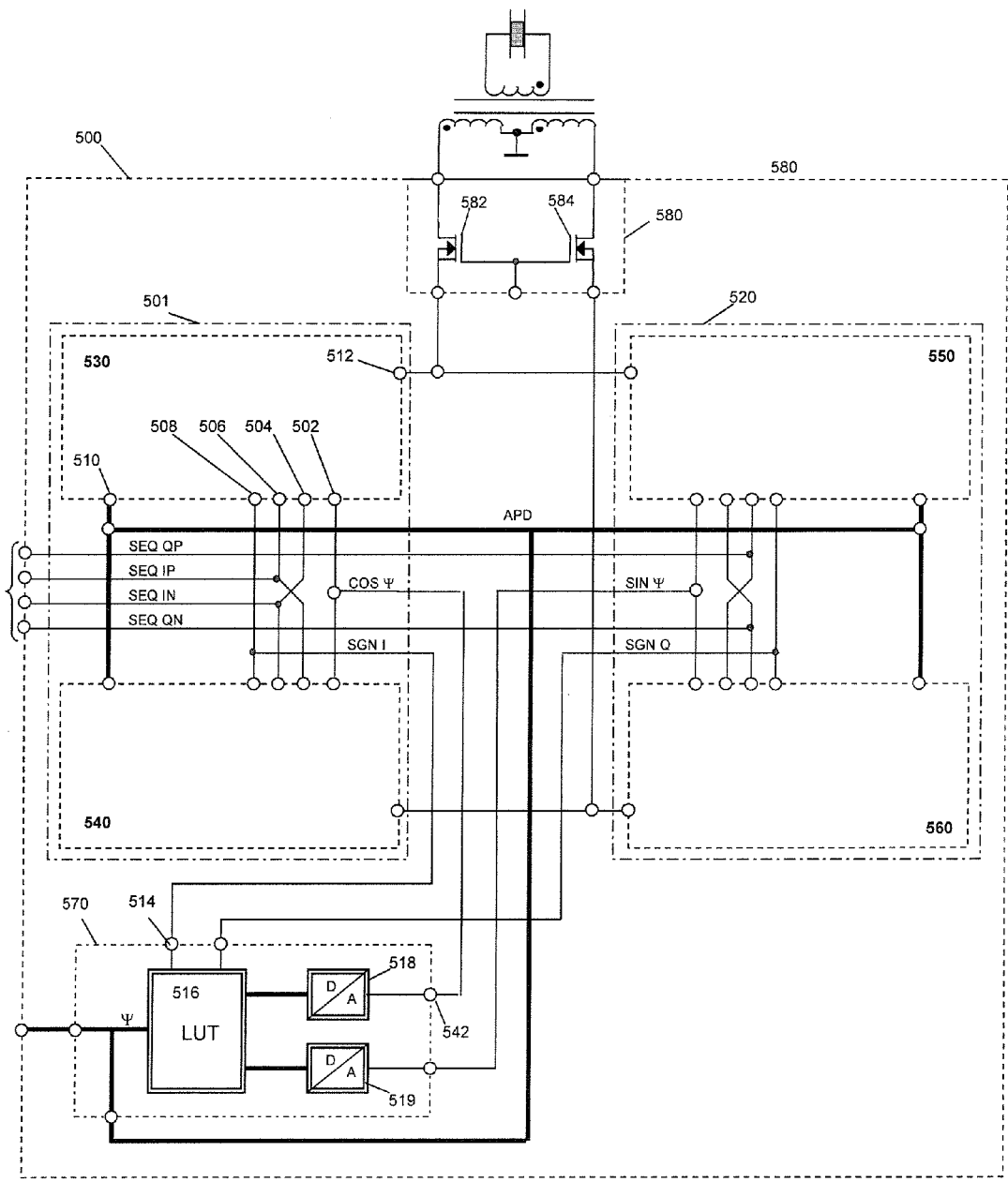
FIG. 5 is a block diagram of another embodiment of an ultrasound transmitter.

FIG. 5 depicts the second embodiment 500 comprises two identical pulse height and width multipliers 501, 520, a transmit controller 570, and an output multiplier 580. Each of the PHWMs 501 and 520 comprises two identical programmable current drivers 530, 540 and 550, 560. Interface and architecture of these drivers are shown in FIG. 7.

Referring to the PHWM 501, the first and second clock terminals 504, 506 of the first and the second drivers are connected in reverse. These terminals are fed by the PWM pulse train as discussed previously.

Switching inputs 508 of the first and second drivers 530, 540 are controlled by the polarity node 514. Reference inputs 502 of the first driver 530 and the second driver 540 are connected together. Voltage at their connection point is defined by one of the phase rotating factors provided by the transmitter controller 570 through the node 542.

Data ports 510 of the current drivers are supplied by the controller 570 altogether. As can be seen, in the second embodiment, the apodization settings are provided in a digital format.

Outputs 512 of the first 530 and second drivers 540 from the first PHWM 501 are respectively connected to the outputs of the first 550 and the second 560 drivers from the second PHWM 520. Then, these signals are applied to a transformer-coupled class B push-pull amplifier 580 having its first 582 and second transistors 584 connected in a common-gate configuration. Consequently, the power amplifier 580 is driven by a sum of the currents produced by both PHWMs.

Referring to the transmit controller 570, LUT 516 converts the input value of the phase angle into the sine and cosine function of said angle feeding afterward two conventional DACs, 518 and 519. Thus, the amplitude of current pulses generated by the PHWMs 501, 520 becomes directly proportional to the sine/cosine rotating factors and inversely proportional to a resistance of the programmable resistor, i.e., to the apodization factor. This partition reduces the phase rotation errors due to the threshold voltage deviation.

Figure 4:
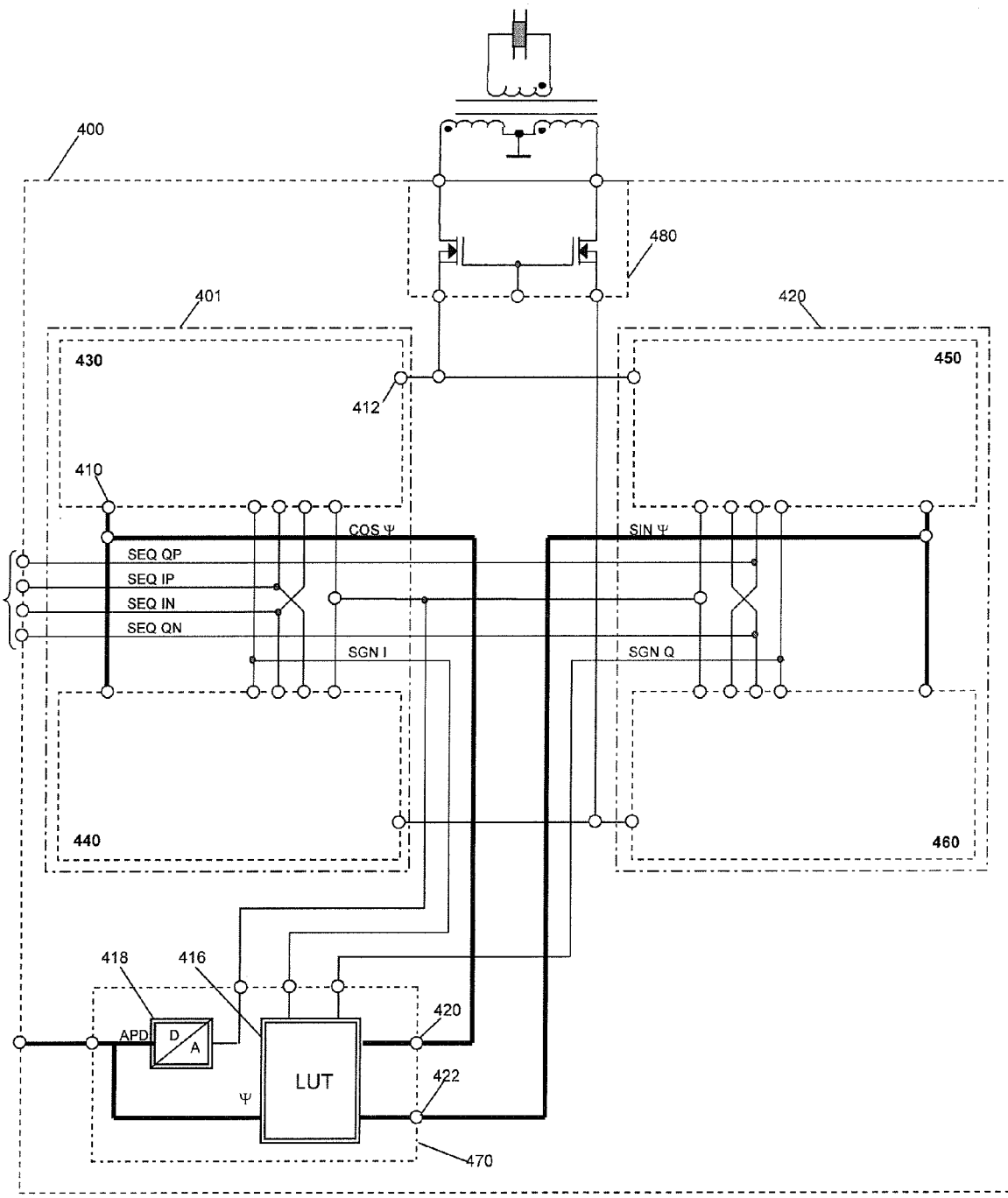
FIG. 4 is a block diagram of an embodiment of an ultrasound transmitter.

A third embodiment shown in FIG. 4 comprises a transmit controller 470 having a LUT 416, a DAC 418, a power amplifier 480, and two identical PHWMs, 401 and 420. The transistor amplifier 480 operates in a common-gate mode providing essentially low input impedance. Each PHWM comprises a pair of programmable current drivers (430 and 440 vs. 450 and 460) aimed to feed the power amplifier 480. The drivers' interconnection within a PHWM duplicates the one discussed in respect of the second embodiment. However, the beamformation data are encoded differently.

In operation, transmit controller 470 receives the apodization settings in a digital format and converts it into analog. Accordingly, the reference nodes 412 are connected altogether with the output of DAC 418.

The phase rotating data are distributed digitally. Referring FIG. 4, LUT 416 feeds the first 420 and the second rotation 422 ports. Agreeably, the phase rotation data are directly applied to the driver's data ports 410 grouped in pairs. Thus, as previously, the PWM pulse train will determine timing of the current pulses produced by a driver. In contrast, the amplitude of these pulses is directly proportional to the apodization settings and inversely proportional to resistance of the DPR, i.e., to the one of phase rotating factors.

If the DPR resistors are binary-weighted as shown in FIG. 7, this programmable current driver can be interpreted as a linear current-output DAC. However, it will be appreciated that its conversion speed is defined by the firing rate rather than by sampling frequency.

Alternatively, to avoid using a LUT, a nonlinear current driver can be implemented. In this architecture, the driver provides both digital-to-analog and trigonometric conversion at the same time. Technically, it can be done by selecting distinct resistors for each switch/resistor cell and increasing the number of cells or by making the cell topology more complicated. Both approaches, however, require extensive hardware resources.

While the invention has been described above by reference to various embodiments, it would be understood that many changes and modifications could be made without departing from the scope of the invention. For example, different multipliers, current drivers, switches, or output amplifier configurations may be used. It is therefore intended that the foregoing detailed description be understood as an illustration of the presently preferred embodiments of the invention, and not as a definition of the invention. It is only the following claims or added claims, including all equivalents, are intended to define the scope of this invention.

What is claimed is:

1. An ultrasound transmit beamformer system comprising:
   a host processor which is a transmit controller, wherein said transmit controller comprises:
   a memory which stores a look-up table, wherein data stored in the look-up table is used to converts an input value of a phase angle into two digital words representing sine and cosine functions of said phase angle;
   a pair of Digital to Analog converters (DAC) attached to the memory which provides multiplication factors for phase rotation of said phase angle; and
   a third DAC for receiving apodization data and for providing a reference voltage for said pair of DACs;
   integrated circuit transmitters coupled to said host processor, wherein said integrated circuit transmitters are a pair of pulse height and width multipliers (PHWMs), wherein each of said pair of PHWMs is attached to a respective one of said pair of DACs, wherein each of the pair of PHWMs comprises a pair of on/off switchable current drivers; and
   a transformer coupled to said pair of PHWMs and driven by said pair of PHWM;
   wherein each of said pair of PHWMs receive a Pulse Width Modulation (PWM) pulse train, each of said pair of PHWMs configured to receive said multiplication factors for phase rotation of said phase angle from said respective one of said pair of DACs and generates signals modulated by said phase rotation data and apodization data, amplitudes of said signals modulated being proportional to a product of said phase-rotating data and said apodization data.

2. The ultrasonic transmit beamformer system of claim 1, wherein said pair of pulse height and width (PHWM) are identical.

3. The ultrasonic transmit beamformer system of claim 1, wherein each of said pair of pulse height and width (PHWM) comprises a pair of identical on/off switchable current drivers.

4. The ultrasonic transmit beamformer system of claim 1, wherein each of said pair of on/off switchable current drivers comprises:
   a multiplexer attached to said PWM pulse train;
   a switching device attached to the multiplexer;
   a resistive element attached to the switching device; and
   an amplifier attached to the resistive element and to said respective one of said pair of DACs.

* * * * *